US009402671B2

(12) United States Patent  (10) Patent No.: US 9,402,671 B2
Donovan  (45) Date of Patent: Aug. 2, 2016

(54) VALVE CONTROL MECHANISM AND METHOD

(71) Applicant: KYPHON SARL, Neuchatel (CH)

(72) Inventor: Brian W. Donovan, San Jose, CA (US)

(73) Assignee: KYPHON SÀRL, Neuchâtel (CH)

( * ) Notice: Subject to any disclaimer, the term of this patent is extended or adjusted under 35 U.S.C. 154(b) by 0 days.

(21) Appl. No.: 14/856,103

(22) Filed: Sep. 16, 2015

(65) Prior Publication Data

US 2016/0000491 A1 Jan. 7, 2016

Related U.S. Application Data

(63) Continuation of application No. 13/738,014, filed on Jan. 10, 2013, now Pat. No. 9,163,749.

(51) Int. Cl.
| | | |
|---|---|---|
| *G05D 7/01* | (2006.01) | |
| *A61B 17/00* | (2006.01) | |
| *A61B 17/88* | (2006.01) | |
| *F16K 31/60* | (2006.01) | |
| *F16K 35/02* | (2006.01) | |

(52) U.S. Cl.
CPC ............ *A61B 17/8822* (2013.01); *F16K 31/602* (2013.01); *F16K 35/022* (2013.01); *G05D 7/01* (2013.01); *A61B 2017/00367* (2013.01); *Y10T 137/0318* (2015.04)

(58) Field of Classification Search
CPC .................... Y10T 137/0318; A61B 17/8822; A61B 2017/00367; F16K 31/602; F16K 35/022; G05D 7/01
USPC ........ 606/92–95; 251/294, 231, 279, 280, 78; 220/470, 473; 239/526, 527, 578
See application file for complete search history.

(56) References Cited

U.S. PATENT DOCUMENTS

| | | | |
|---|---|---|---|
| 3,185,435 | A * | 5/1965 | Hauser .................... F16K 3/184 251/158 |
| 5,368,386 | A | 11/1994 | Murray |
| 5,514,135 | A | 5/1996 | Earle |
| 6,083,229 | A | 7/2000 | Constantz et al. |
| 6,149,655 | A | 11/2000 | Constantz et al. |
| 7,744,270 | B2 | 6/2010 | Plishka et al. |
| 7,946,417 | B2 | 5/2011 | Plishka et al. |
| 8,021,037 | B2 | 9/2011 | Krueger et al. |

\* cited by examiner

*Primary Examiner* — John K Fristoe, Jr.
*Assistant Examiner* — Daphne M Barry
(74) *Attorney, Agent, or Firm* — Martin & Ferraro LLP (57) ABSTRACT

A valve controller includes a housing, and a lever extending from the housing. The lever includes a protrusion rigidly attached to the lever, and the lever is biased to an initial position. A switch has an open and a closed position. A linkage is pivotally connected to the switch, and the linkage includes a centrally disposed slot configured to receive the protrusion such that movement of the switch controls movement of the linkage and the lever such that moving the switch to the closed position closes a valve controlled by the lever regardless of a position of the lever.

16 Claims, 6 Drawing Sheets

VALVE CONTROL MECHANISM AND METHOD

This application is a continuation of application Ser. No. 13/738,014, filed Jan. 10, 2013, all of which is incorporated herein by reference.

TECHNICAL FIELD

The present disclosure generally relates to medical devices for dispensing fluids and fluidized solids, and more particularly to a value control device, system and method for dispensing cement for surgical applications.

BACKGROUND

Many medical procedures employ medical grade cement in connection with the restoration and strengthening of bone structures. During such procedures, cement is typically dispensed to a bone to fill in voids or spaces in the bone or between medical devices or implants attached to or embedded within the bone. These dispensing devices may include systems as simple as syringes and as complex as electronically controlled valves.

Due to the medical nature of some procedures, the amount and placement of the fluids, such as, cement, needs to be supervised carefully. Despite the simplicity or complexity of the dispensing system, control over when, where and how much cement is dispensed is of concern. This disclosure describes improvements over these prior art technologies in providing better control for dispensing fluids, in particular, with respect to applications where greater valve control is needed.

SUMMARY

Accordingly, a device, system and method for controlling a valve are provided. In one embodiment, in accordance with the principles of the present disclosure, a valve controller is provided. The valve controller comprises a housing, and a lever extending from the housing and pivotally connected thereto to control a valve. The lever includes a protrusion rigidly attached to the lever, and the lever is biased to an initial position. A switch has an open position and a closed position. The switch is pivotally connected to the housing. A linkage is pivotally connected to the switch, and the linkage includes a centrally disposed slot configured to receive the protrusion such that movement of the switch controls movement of the linkage and the lever such that moving the switch to the closed position closes a valve controlled by the lever regardless of a position of the lever.

In one embodiment, the valve controller comprises a housing and a lever extending from the housing and pivotally connected thereto to control a valve. The lever includes a protrusion rigidly attached to the lever, and the lever is biased to an initial position by a tension cable. A switch has an open position and a closed position. The switch is pivotally connected to the housing at a centrally disposed pivot point, and the linkage is pivotally connected to the switch at an end portion. A linkage is pivotally connected to the switch, and the linkage includes a centrally disposed slot configured to receive the pin such that movement of the switch controls movement of the linkage and the lever wherein moving the switch to the closed position closes a valve controlled by the lever regardless of a position of the lever. The slot is dimensioned and configured to: engage the protrusion to permit full extension of the lever in the initial position and permit the linkage to rotate about a pivot point connected to the switch when the lever is activated; move the switch from the closed position to the open position upon activation of the lever; cause the lever that has been activated to be stopped and in need of resetting, when the switch is moved from the open position to the closed position; and cause the switch to move from the open position to the closed position at an end of a stroke of the lever where the lever is maintained at the end of the stroke of the lever until the switch is moved to the open position.

In one embodiment, a method for controlling a valve is provided. The method comprises the steps of: providing a valve controller having a housing; a lever extending from the housing and pivotally connected thereto to control a valve, the lever including a protrusion rigidly attached to the lever and being biased to an initial position; a switch having an open position and a closed position, the switch being pivotally connected to the housing; and a linkage pivotally connected to the switch, the linkage including a centrally disposed slot configured to receive the protrusion such that movement of the switch controls movement of the linkage and the lever; closing the valve upon one of releasing the lever or switching the switching to the closed position regardless of a position of the lever; and permitting the valve to be opened upon activating the lever.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of a valve control mechanism and related methods of use are disclosed and discussed in terms of medical devices for the treatment of musculoskeletal disorders and more particularly, in terms of a value control handle mechanism and method for dispensing cement for the repair or strengthening of bone structures. It is envisioned that the system and method may be employed in applications such as correction of cracks, fissure, voids, such as, due to osteoporosis or other diseases or injuries. In addition, the system and method may be employed with the placement of support structures or devices attached to or embedded within bone. For example, such structures may include pins, screws, hip replacement joints, knee replacement joints, elbow replacement joints, shoulder replacement joints, etc.

In one embodiment, the system and method include a mechanism, which is part of a handle or lever system. The lever system is employed by a technician or surgeon and is connected by tension cables or other biasing device to a remote pump. The valve may be opened or closed based open displacement of the tensioned cable. The displacement of the tension cable is provided by a stroke of the lever. In one embodiment, the pump may be employed for dispensing cement or other medically useful fluid. The mechanism controls the actuation of a valve in the pump that stops and starts flow of the cement out of the pump. The mechanism operates to permit the valve of the pump to be closed regardless of a position of the handle or lever throughout its stroke. This is achieved using a switch, such as a rocker switch, which interacts with the lever of the mechanism such that the valve and therefore the flow of fluid (cement) can be stopped using the rocker switch regardless of the position of the handle. The mechanism also permits the valve to automatically open when an operator again squeezes the lever even if the switch is in the closed position (e.g., the mechanism shifts the switch automatically). The mechanism therefore provides improvements in dispensing control. Details of illustrative embodiments will be described herein.

It is contemplated that one or all of the components of the valve control mechanism may be provided by disposable, peel-pack, pre-packed sterile devices. One or all of the components of the valve control mechanism may be reusable. The valve control mechanism may be configured as a kit with multiple sized and configured components.

It is envisioned that the present disclosure may be employed as part of a treatment procedure for the treatment of bone disorders or injuries, such as, for example, osteoporosis, bone fractures, bone breaks, bone reconstruction, joint replacement and other injuries or abnormalities. It is contemplated that the present disclosure may be employed with other osteal and bone related applications, including those associated with diagnostics and therapeutics. The systems and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a system, mechanism and related methods of employing the system and mechanism in accordance with the principles of the present disclosure. Alternate embodiments are also disclosed. Reference will now be made in detail to the exemplary embodiments of the present disclosure, which are illustrated in the accompanying figures. Turning now to FIGS. 1-6, there are illustrated components of a valve control system, such as, for example, a hand controllable valve controller 10 in accordance with the principles of the present disclosure.

Figure 1:
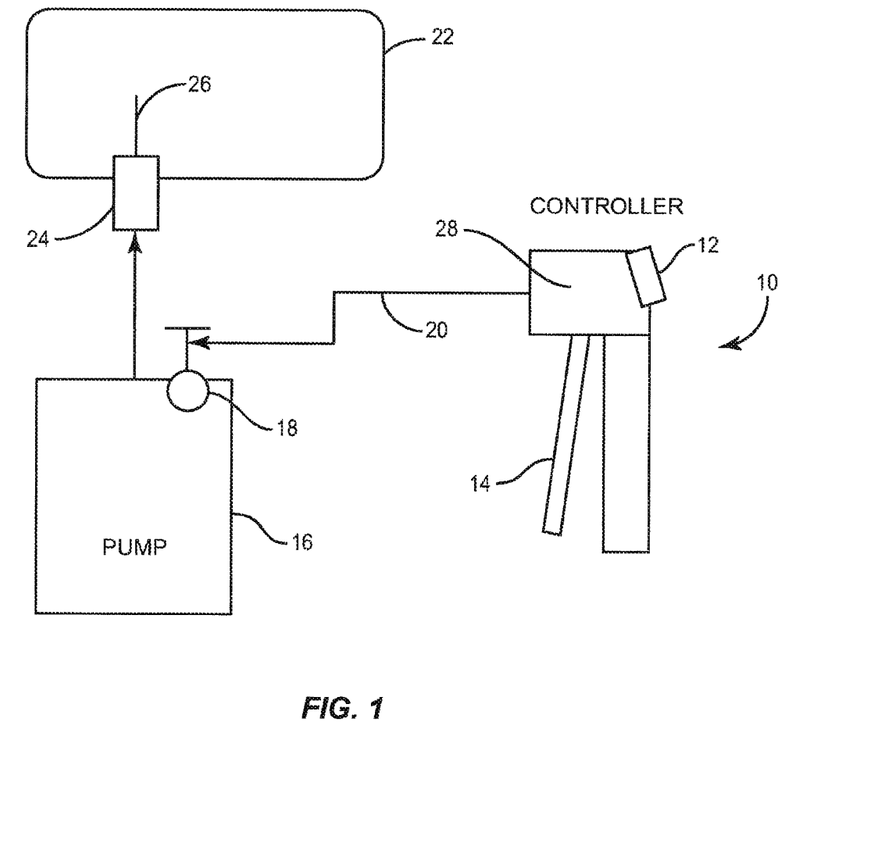
FIG. 1 is a schematic diagram showing a valve controller of one embodiment of components of a system in accordance with the principles of the present disclosure.

Referring to FIG. 1, a schematic diagram generally depicts the valve controller 10 in an operational environment. The valve controller or controller 10 includes a mechanism 28 coupled to a handle or lever 14. The mechanism 28 connects to one or more tension cables 20 to a remote pump 16. The mechanism 28 controls actuation of a valve 18 in the pump 16 that stops and starts flow of fluid out of the pump 16. The mechanism 28 operates to permit the valve 18 to be closed regardless of position of the lever 14. The mechanism 28 permits the valve to automatically open when the operator squeezes the lever 14 connected to the tension cable (70, FIG. 3B). A state of the mechanism 28 is adjusted in accordance with a switch 12 (e.g., a rocker switch) or other mechanical switch or mechanism. Motion of the switch 12 provided sufficient displacement to permit proper motion of the mechanism 28 to achieve a plurality of modes of operation.

In one embodiment, the controller 10 enables/disables the valve 18 to dispense fluid to a dispensing device 24. The dispensing device 24 may include a dispensing nozzle 26 to dispense the fluid on or within a subject. In a particularly useful embodiment, the fluid may include cement, epoxy or other fluidized solid media to be applied during a surgical procedure, and in particular applied to bone for the treatment or prevention of disease or injury. It should be understood that the controller 10 may be employed in other dispensing systems, with other dispensing media, and for other applications. The dispensing nozzle 26 may include a needle or other shaped orifice for accurately dispensing the fluid. It should be understood that the environment depicted in FIG. 1 is for illustrative purposes and may include additional or different components from those shown. For example, components such as e.g., pressure regulators, additional valves, piping, monitoring or imaging equipment, reservoirs, etc. may also be employed. The environment depicted in FIG. 1 may be included in a portable handheld system or may include a large stationary dispensing system.

Figure 2:
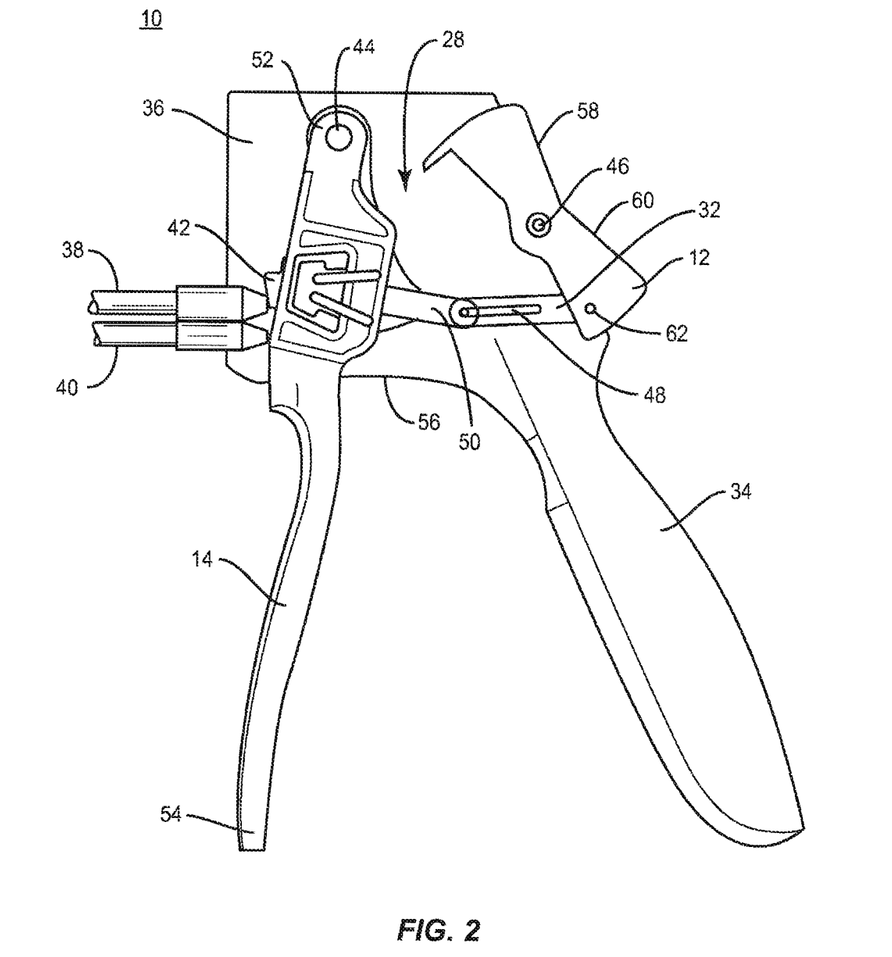
FIG. 2 is a side view of the valve controller of the system shown in FIG. 1 with a housing depicted in phantom to show an internal mechanism in accordance with the principles of the present disclosure.

Referring to FIG. 2, controller 10 is shown in greater detail in accordance with one illustrative embodiment. Controller 10 includes a housing 36 (depicted in phantom to view internal components). Housing 36 provides mounting positions for the mechanism 28 included therein.

It is envisioned that housing 36 may have various surface configurations, such as, for example, rough, porous, semi-porous, dimpled, polished and/or textured according to the requirements of a particular application. It is further contemplated that housing 36 may have various shapes or cross sectional configurations, such as, for example, oval, oblong, triangular, rectangular, square, polygonal, irregular, uniform, non-uniform, variable, tapered, etc.

Housing 36 receives rigid or flexible pipe ends 38 and 40 therein. Pipe ends 38 and 40 have adapted end portions configured to be received through the housing 36. Pipe ends 38 and 40, if rigid, provide stabilization for a position of the controller 10. The pipe ends 38 and 40 illustratively show a portion of piping that connects with a valve and pump (see FIG. 1). The pipe ends 38 and 40 may each include a tension cable therein which will have its function described herein after.

Pipe end 38 includes a tensioned cable (not shown), which is affixed to a support member 42. The support member 42 may include a cable termination that is mounted in or to the support member 42 to provide a force to stabilize the controller 10 during use. Pipe end 40 also includes a tensioned cable (not shown), which is employed to open or close the valve (18, FIG. 1). Support member 42 is connected to or mounted in the housing 36. Support member 42 may be supported using a dowel or pin 44 and may have other connection points.

A movable handle, lever or trigger 14 includes a first end portion 52 that is pivotally connected to the housing 36 through the dowel or pin 44. The lever 14 further includes a free end portion 54, which is configured to rotatably move to control the valve for dispensing fluid. For example, to select the valve position as open or closed, an operator squeezes (activates) or relaxes tension on a tension cable (through pipe end 40) using the lever 14. The lever 14 is capable of moving within a slot or opening 56 formed in the housing 36. The lever 14 is squeezed using a grip or handle 34, which may be integrally formed with the housing 36. The grip 34 functions as a frame to provide support and react to imparted loads through the controller 10. The lever 14 may include a lever link 50 integrally formed with the lever 14, or the lever link 50 may be configured as a separate part and rigidly connected to the lever 14. The lever link 50 rotates with the lever 14. The lever link 50 includes a pin or protrusion 64 extending from a lateral portion of the lever link 50.

A switch 12, such as, e.g., a rocker switch, is pivotally connected to the housing 36 with a pivot pin or axis 46. In the embodiment depicted, switch 12 is rotatable between two positions. One position includes an open valve setting (open) and the other includes a closed valve setting (closed). The switch 12 includes an upper surface 58 and a lower surface 60. When the upper surface 58 is depressed, the switch 12 moves into the housing 36 at the upper surface 58, and the lower surface 60 of the switch moves outward from the housing 36. When the lower surface 60 is depressed, the switch 12 moves into the housing 36 at the lower surface 60, and the upper surface 58 of the switch moves outward from the housing 36.

A switch linkage 32 is pivotally coupled to a lower portion of the switch 12 by a pivot joint 62, although this joint 62 may be connected to an upper portion of the switch 12 with the appropriate changes to the mechanism 28. The switch linkage 32 includes a slot 48 or similar structure, which receives the protrusion 64 of the handle linkage bar 50 to form a pin-in-slot joint. The interactions between the lever 14, the lever link 50, the switch linkage 32 and the switch 12 provide different configurations, which correspond to a plurality of modes or operations provided by the controller 10, which will be described in greater detail hereinafter.

Although the components of the valve controller 10 are not usually inserted or embedded in the body, it may still be advantageous to provide components that are biologically acceptable materials suitable for medical applications. The biologically acceptable materials suitable for medical applications for the components of the valve controller 10 can be fabricated from and include metals, synthetic polymers, ceramics and bone material and/or their composites, depending on the particular application and/or preference of a medical practitioner. For example, the components of the valve controller 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, and their combinations. Various components of the valve controller 10 may have material composites, including the above materials, to achieve various desired characteristics such as strength, rigidity, elasticity, compliance, mechanical performance and durability. The components of the valve controller 10, individually or collectively, may also be fabricated from a heterogeneous material such as a combination of two or more of the above-described materials. The components of the valve controller 10 may be monolithically formed, integrally connected or include fastening elements and/or instruments, as described herein. Valve controller 10 may be employed during, for example, an open, mini-open or minimally invasive surgical technique to apply cement to attach an element to a bone or to fill voids cracks, etc. in bone, or other applications.

The mechanism 28 has illustrative operating modes, which will be described in greater detail with reference to FIGS. 3A-3C (Mode 1), FIGS. 4A-4C (Mode 2), FIGS. 5A-5C (Mode 3) and FIG. 6 (Mode 4) to provide an exemplary understanding of the present principles. The modes depicted show configurations that permit the activation of the lever 14 and the switch 12 and the corresponding motion that achieves the aim of providing the resetting of a valve regardless of the position of the lever 14. Other modes and different configurations of these modes are also contemplated.

Figure 3A:
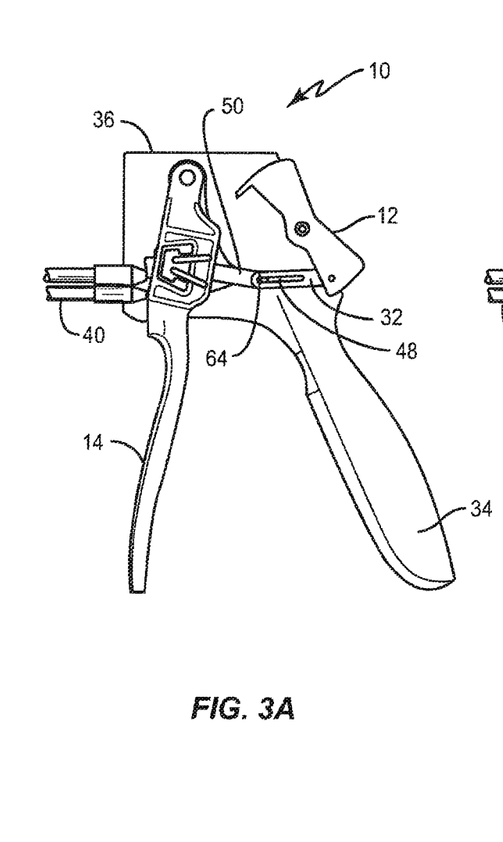
FIGS. 3A-3C are side views of the valve controller showing a lever being activated while a switch is in an open position in accordance with one mode of operation.
Figures 3B, 3C:
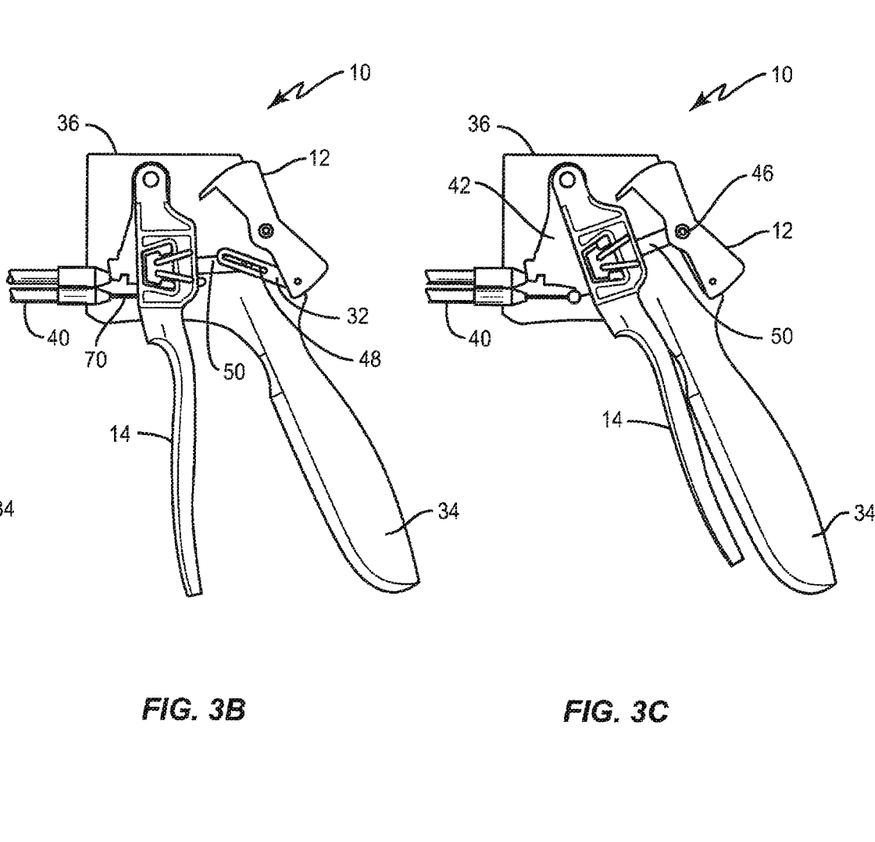

Referring to FIGS. 3A-3C, Mode 1 operation of controller 10 is illustratively shown. Mode 1 is associated with the switch 12 set to a valve open condition or state throughout FIGS. 3A-3C. Switch 12 is initially in a valve open position, which corresponds to the upper portion 58 of the switch 12 being depressed. As the lever 14 is squeezed (FIGS. 3B and 3C), a tension cable 70 is pulled through the pipe end 40 and the lever link 50 moves in the direction of the switch linkage 32. It is contemplated that tension cable 70 may be braided, such as a rope and provide a predetermined force resistance. The pin or protrusion 64 moves freely along the slot 48 but does not interact with the switch 12. The deflection of the lever 14 and therefore the lever link 50 are accommodated first by the length of the slot 48, then by rotating upward into/toward the switch 12 (FIG. 3B).

The pin 64 first moves in the slot 48 to a centrally located position, the movement of the lever 14 causes the switch linkage 32 to rotate upward and then the pin 64 eventually begins to move in the slot 48 in the opposite direction of its initial movement. The switch linkage 32 moves upward into the switch 12 (FIG. 3C). The switch 12 remains in the valve open position throughout the rotation of the lever 14 due to the rotation and play provided by the slot 48 in the switch linkage 32. The pulling of the tension cable 70 opens the valve 18 (FIG. 1) so that fluid (e.g., cement) may be dispensed.

Figure 4A:
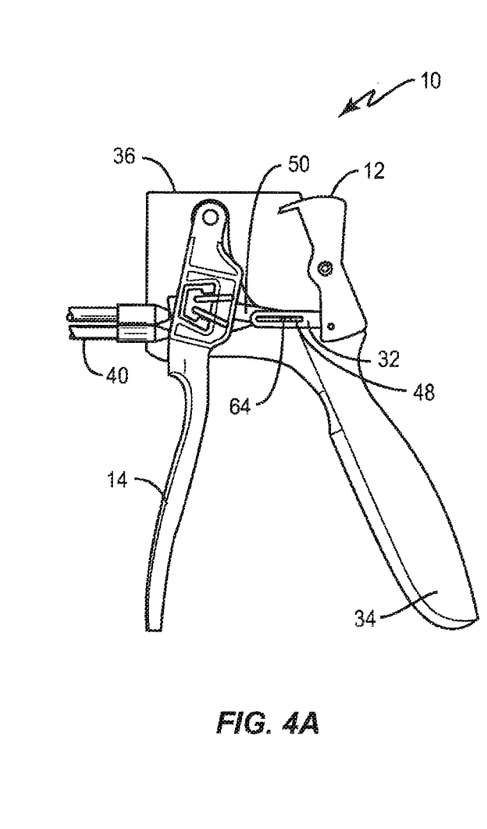
FIGS. 4A-4C are side views of the valve controller showing the lever being activated to set the switch to an open position for a closed position in accordance with another mode of operation.
Figure 4B:
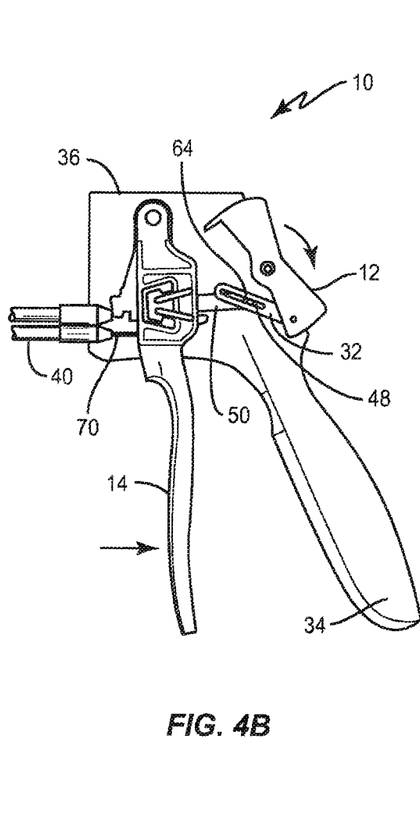
Figure 4C:
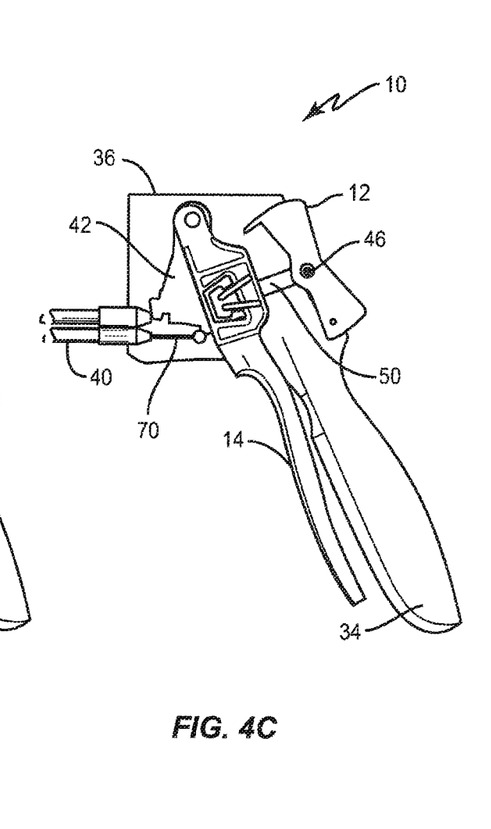

Referring to FIGS. 4A-4C, Mode 2 operation of controller 10 is illustratively shown. Mode 2 is associated with the switch 12 initially set to a valve closed condition or state (FIG. 4A), but the lever 14 is biased open by the tension of cable 70 and fluid is not yet being dispensed. As the lever 14 is squeezed (FIGS. 4B and 4C), the lever linkage 50 rotates the switch linkage 32 (as before in FIG. 3C), and the switch 12, pinned to the switch linkage 32 at its lower position, is moved into the open position (FIG. 4B). As the lever 14 is further squeezed, the switch linkage 32 is moved into the switch 12 (FIG. 4C), which may be hollow to receive the linkages 32 and 50.

Figure 5A:
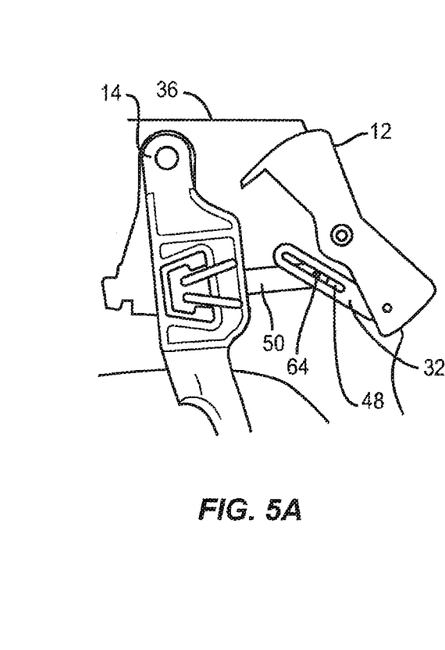
FIGS. 5A-5C are side views of the valve controller showing the switch set to a closed position while the lever is being activated to force the lever to be reset before a valve controlled by the lever can be reopened in accordance with another mode of operation.
Figure 5B:
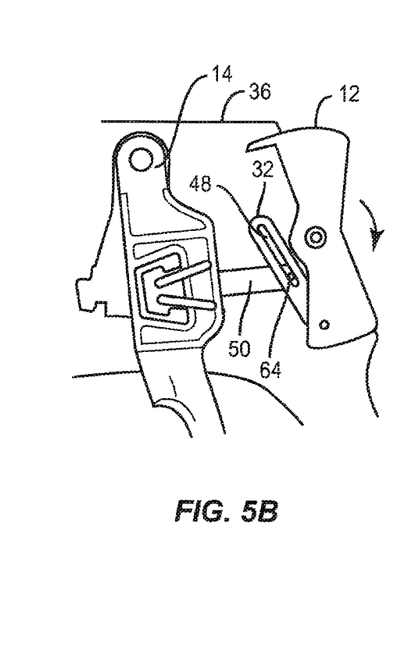
Figure 5C:
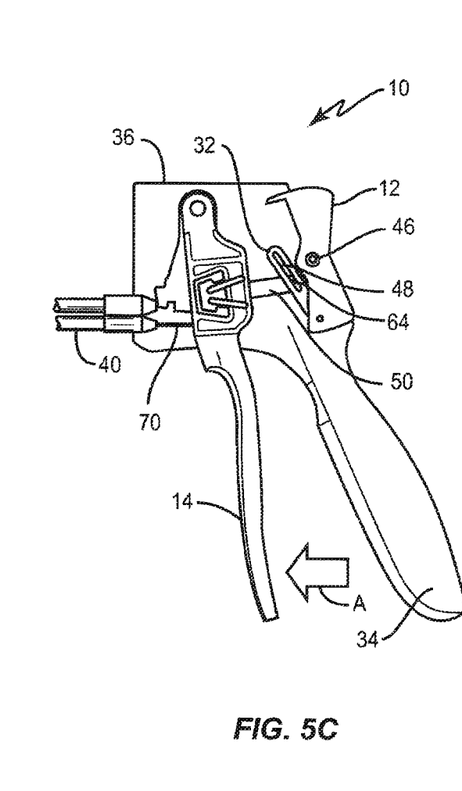
Figure 6:
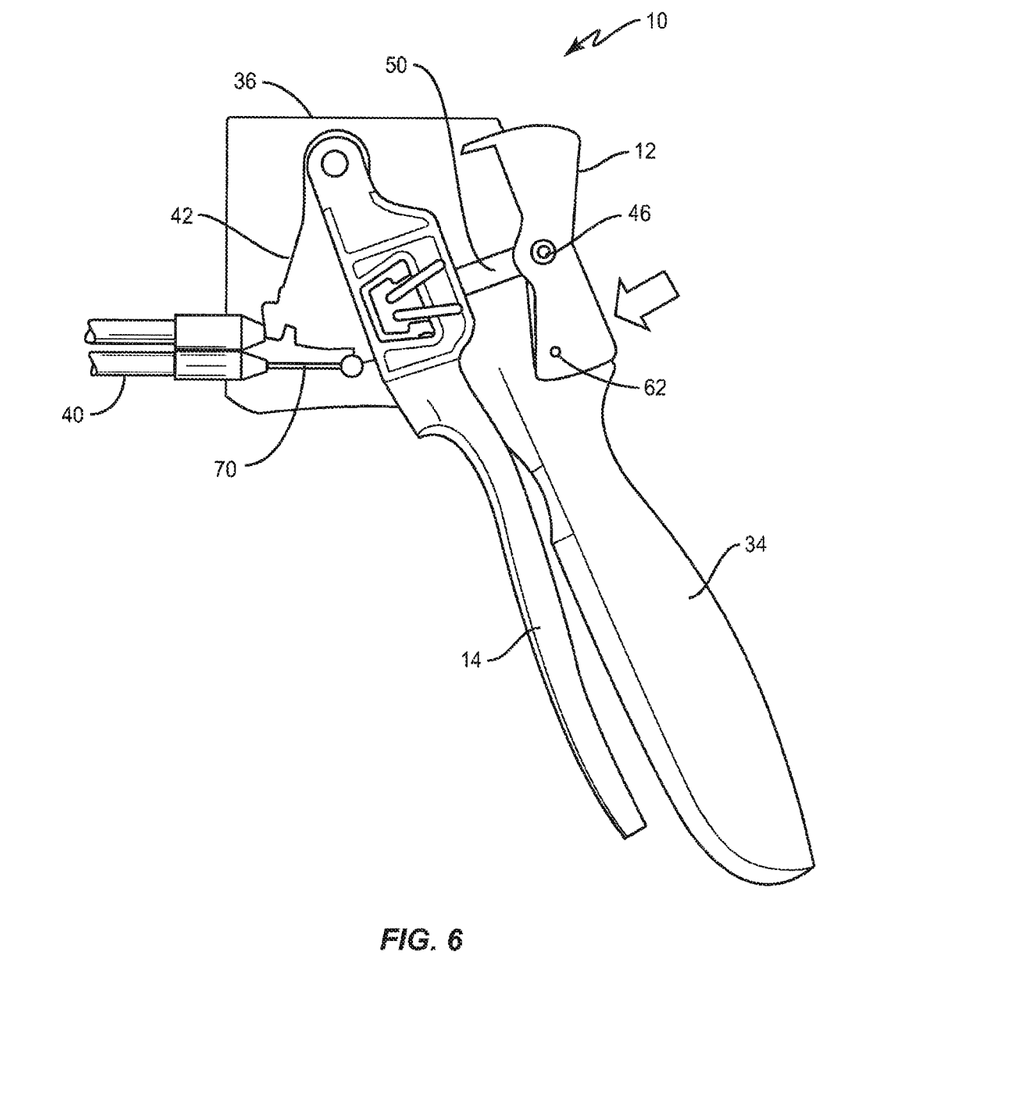
FIG. 6 is a side view of the valve controller showing the switch set to the dosed position upon reaching an end of stroke for the lever in accordance with another mode of operation.

Referring to FIGS. 5A-5C, Mode 3 operation of controller 10 is illustratively shown. Mode 3 is associated with the switch 12 set to a valve open condition or state (FIG. 5A) and switched to the valve closed state (FIG. 5B) while the lever 14 is partially squeezed and fluid is being dispensed. While lever 14 is partially squeezed, the switch 12 is moved by the operator to the valve closed position (FIG. 5B). As the switch 12 is moved, the pin 64 on the lever linkage 50 is pushed through a flexible stop on the switch linkage 32. The mechanism 28 then needs to be reset by moving the lever 14 to its full forward position in the direction of arrow "A" before dispensing can continue (FIG. 5C). This forces a reset condition for the valve before restarting the dispensing of fluid and hence the valve can be closed using the switch 12 and the mechanism 28 despite the position of the lever 14. Referring to FIG. 6, Mode 4 operation of controller 10 is illustratively shown. Mode 4 is associated with the switch 12 being freely movable. When the lever 14 is fully squeezed (e.g., at the end of its stroke), the switch 12 is still free to move. However, lever 14 will not move forward unless the switch 12 is in the open position. In this mode, the linkage 32 is stowed in the switch 12 and the pin 64 in the slot 48 is substantially coincident with the pivot 46 of the switch 12 when the switch 12 is in the closed position. In this way, the tension of cable 70 is in equilibrium against the pin 46 leaving the lever 14 in its full stroke position until the switch 12 is moved to the open position. By moving, the switch 12 to the open position, the pin 64 slides down slot 48 releasing the lever 14, which is pulled back by the tension of cable 70.

The mechanism 28 permits automatic reset of the flow valve 18 when used in a fluid delivery system (e.g., mechanical cement). When the switch 12 is in the open position, the level can be squeezed to dispense fluid without affecting the switch (Mode 1). When the switch 12 is in a closed position and the lever 14 is squeezed, the switch 12 is switched to open (Mode 2). When the switch 12 is turned to the closed position while the lever 14 is squeezed, the release of the lever 14 will reset the switch 12 to closed (Mode 3). When the lever 14 is at full stroke, the switch 12 closes and the lever 14 is released when the switch 12 is moved to an open position (Mode 4). These modes are illustrative to demonstrate exemplary usage of one exemplary embodiment. Other modes and configurations are also contemplated that can achieve valve control using a switch and providing for closure of the valve regardless of an activation position of a lever used to open the valve.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A valve controller, comprising:
 a housing;
 a lever extending from the housing and pivotally connected thereto to control a valve, the lever including a protrusion rigidly attached thereto, and the lever being biased to an initial position;
 a switch having an open position and a closed position, the switch being pivotally connected to the housing; and
 a linkage pivotally connected to the switch, the linkage including a centrally disposed slot configured to receive the protrusion such that movement of the switch controls movement of the linkage and the lever wherein moving the switch to the closed position closes a valve controlled by the lever regardless of a position of the lever.

2. A valve controller as recited in claim 1, wherein the lever is biased toward the initial position by a tension cable.

3. A valve controller as recited in claim 1, wherein a tension cable mechanical controls the valve.

4. A valve controller as recited in claim 1, wherein the switch includes a rocker switch having a first end portion and a second end portion opposite the first end portion, wherein when the rocker switch is moved in a direction toward the housing at the first end portion, the rocker switch is in the open position and when the rocker switch is moved in a direction toward the housing at the second end portion, the rocker switch is in the closed position.

5. A valve controller as recited in claim 4, wherein the rocker switch is pivotally connected to the housing at a centrally disposed pivot point and the linkage is pivotally connected to the rocker switch at the second end portion.

6. A valve controller as recited in claim 1, wherein the slot is dimensioned and configured to engage the protrusion to permit full extension of the lever in the initial position and permit the linkage to begin to rotate about a pivot point connected to the switch when the lever is activated.

7. A valve controller as recited in claim 1, wherein the slot is dimensioned and configured to move the switch from the closed position to the open position upon activation of the lever.

8. A valve controller as recited in claim 1, wherein the slot is dimensioned and configured to cause the lever that has been activated to be stopped and in need of resetting when the switch is moved from the open position to the closed position.

9. A valve controller as recited in claim 1, wherein the slot is dimensioned and configured to cause the switch to move from the open position to the closed position at an end of a stroke of the lever.

10. A valve controller as recited in claim 9, wherein the lever is maintained at the end of the stroke of the lever until the switch is moved to the open position.

11. A valve controller as recited in claim 1, wherein the housing includes a grip extending along the lever to provide a frame against which the lever can be actuated.

12. A valve controller as recited in claim 1, wherein the valve controls dispensing of cement for a medical procedure.

13. A valve controller as recited in claim 1, wherein the housing includes an opening from which the lever extends.

14. A valve controller as recited in claim 1, further comprising a pump configured to pump liquid through the valve.

15. A valve controller, comprising:
 a housing;
 a lever extending from the housing and pivotally connected thereto to control a valve, the lever including a protrusion rigidly attached to the lever and being biased to an initial position by a tension cable;
 a switch having an open position and a closed position, the switch being pivotally connected to the housing at a centrally disposed pivot point and the linkage being pivotally connected to the switch at an end portion;
 a linkage pivotally connected to the switch, the linkage including a centrally disposed slot configured to receive the protrusion such that movement of the switch controls movement of the linkage and the lever wherein moving the switch to the closed position closes a valve controlled by the lever regardless of a position of the lever, and wherein the slot is dimensioned and configured to:
  engage the protrusion to permit full extension of the lever in the initial position and permit the linkage to rotate about a pivot point connected to the switch when the lever is activated;
  move the switch from the closed position to the open position upon activation of the lever;
  cause the lever that has been activated to be stopped and in need of resetting, when the switch is moved from the open position to the closed position; and
  cause the switch to move from the open position to the closed position at an end of a stroke of the lever where the lever is maintained at the end of the stroke until the switch is moved to the open position.

16. A method for controlling a valve, the method comprising the steps of:
 providing a valve controller having a housing; a lever extending from the housing and pivotally connected thereto to control a valve, the lever including a protrusion rigidly attached to the lever and being biased to an initial position; a switch having an open position and a closed position, the switch being pivotally connected to the housing; and a linkage pivotally connected to the switch, the linkage including a centrally disposed slot configured to receive the protrusion such that movement of the switch controls movement of the linkage and the lever;
 closing the valve upon one of releasing the lever or switching the switch to the closed position regardless of a position of the lever; and
 permitting the valve to be opened upon activating the lever.

* * * * *